United States Patent [19]

Kenna

[11] Patent Number: 4,755,183
[45] Date of Patent: Jul. 5, 1988

[54] LIGAMENT PROSTHESIS
[75] Inventor: Robert V. Kenna, Saddle River, N.J.
[73] Assignee: Pfizer Hospital Products Group, Inc., New York, N.Y.
[21] Appl. No.: 12,409
[22] Filed: Feb. 9, 1987
[51] Int. Cl.⁴ .............................................. A61F 2/08
[52] U.S. Cl. ...................................................... 623/13
[58] Field of Search ........................................... 623/13
[56] References Cited
U.S. PATENT DOCUMENTS
3,953,896  5/1976  Treace ................................... 623/13
4,187,558  2/1980  Dahlen ................................... 623/13

Primary Examiner—Richard J. Apley
Assistant Examiner—James Prizant
Attorney, Agent, or Firm—Peter C. Richardson; Lawrence C. Akers; Elizabeth O. Slade

[57] ABSTRACT

A prosthesis for an anterior cruciate ligament features first and second elongate members, first and second separately tensionable cords, a catch means on the bore surface of each elongate member, and a means for securing the elongate members to the femur and tibia, respectively. The prosthesis has the significant advantage of being able to replace and to perform in substantially the same manner as a natural anterior cruciate ligament. The separate tensioning followed by fixing of the two cords in the implanted prosthesis results in a substantially smoother and more stable range of motion than has been possible with prior art prostheses.

6 Claims, 3 Drawing Sheets

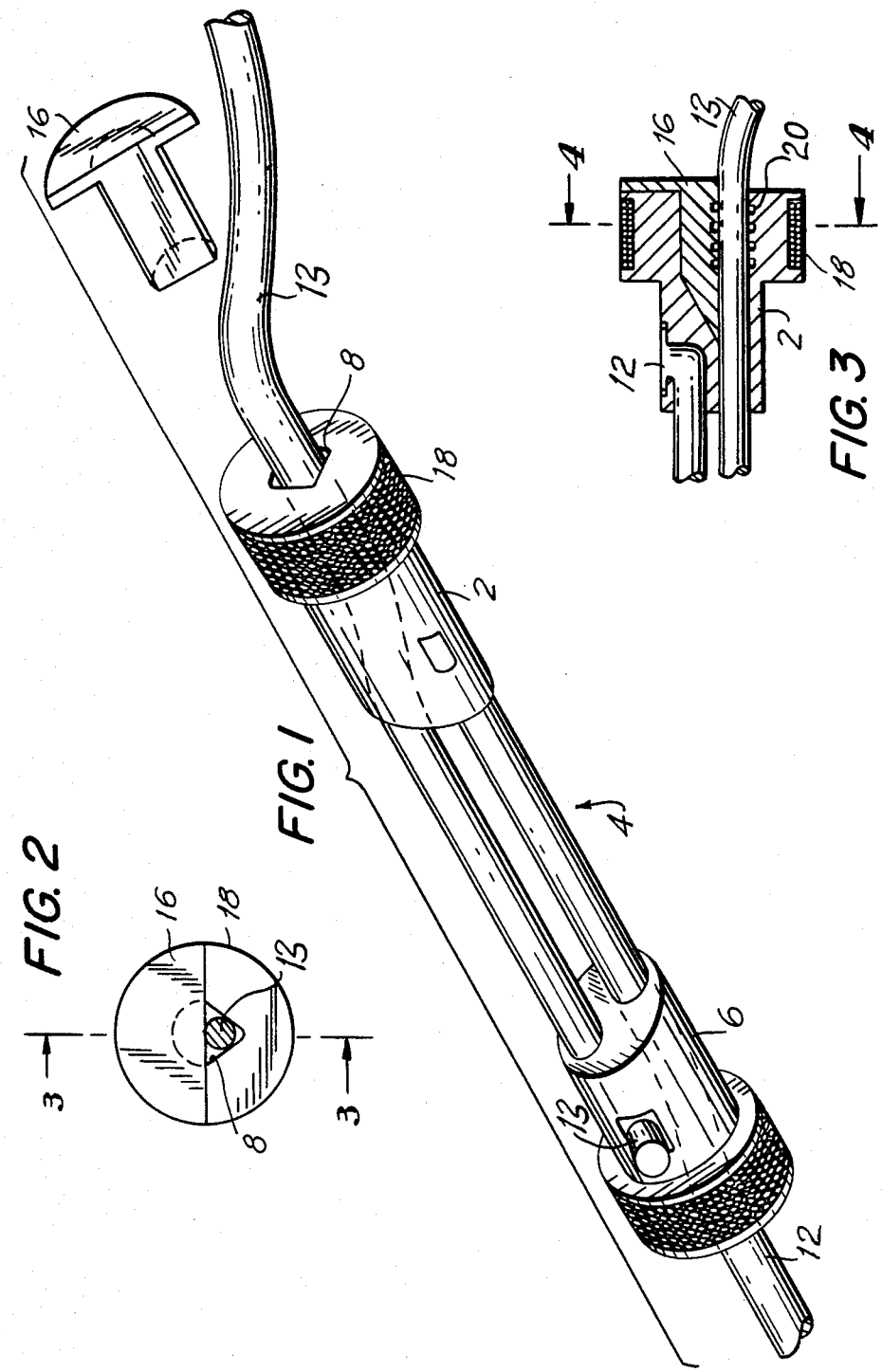

LIGAMENT PROSTHESIS

BACKGROUND OF THE INVENTION

A variety of prostheses have been proposed for the repair or replacement of diseased or damaged ligaments, in particular the anterior cruciate ligament.

U.S. Pat. No. 4,605,414 discloses a process for such a repair wherein the damaged ligament is removed and a strip of patellar tendon is combined with a sleeve of synthetic biocompatible material thereby creating the new anterior cruciate ligament.

U.S. Pat. No. 4,597,766 discloses a ligament replacement which is comprised of a naturally occurring ligament or tendon isolated from an animal source tanned with a bifunctional reagent capable of crosslinking biological tissue. The ligament is fixed in place by attachment of a dicalcified chip of bone which is shaped to receive and retain the bioprosthesis.

U.S. Pat. No. 3,953,896 discloses a prosthetic ligament used to replace a damaged cruciate ligament. In this patent, the prosthetic ligament includes a cylindrical central portion of polyethylene and threaded outer portions provided with bushings to protect the central portion from abrasion caused by skeletal flexing. Fasteners, in the form of nut members, are also provided to fasten the prosthesis within the skeletal apertures.

U.S. Pat. No. 3,545,008 discloses a tendon prosthesis which consists of a Dacron mesh sleeve sutured to the proximal ends of a ruptured tendon. The sleeve includes a mesh netting at its outer ends to encourage fibroblastic infiltration to occur between the severed ends of the tendon for anchoring the prosthesis to the tendon.

U.S. Pat. No. 4,187,558 relates to a prosthetic ligament positioned within a surgically prepared passageway in the bone, and a Dacron or Dacron and silicone strand is disclosed as a replacement for a cruciate ligament with Dacron velour fabric used as collars at the outer ends of the central portion of the prosthesis to promote new tissue growth.

U.S. Pat. No. 3,797,047 discloses an artificial tendon material which consists of a tubular sheath of silicone elastomer with an inner tensile element of knitted fabric.

U.S. Pat. No. 3,805,300 discloses a tendon which is composed of a cord-like combination of silicone and Dacron strip with transverse openings for the natural tendon to be woven therethrough.

In these prior art procedures are well documented the various problems and possible solutions for the repair and/or replacement of the anterior cruciate ligament. A major problem that the prior art has not solved is how to make a replacement anterior cruciate ligament perform in substantially the same manner as the natural anterior cruciate ligament.

The prosthesis of the present invention is placed in the appropriate position to reproduce the femoral and tibial anterior cruciate ligament origins, and then tensioned to approximate the anterior and posterior fibers of the normal anterior cruciate ligament. The result is a substantially smoother and more stable natural range of motion in a knee of a patient.

SUMMARY OF THE INVENTION

The prosthesis of the present invention overcomes the technical, surgical and practical shortcomings of the prior art. An important feature of the present invention is the ability to separately tension the first and second cords to more closely duplicate the function of the normal knee. A further important feature is that the cords, once tensioned, are fixed in the knee so that there is no backward movement of the tensioned cords.

The device of the present invention combines all of these features in one prosthetic device. These features, and other features discussed hereinafter, result in a prosthesis which is dynamically stable and therefore promotes smoother and more natural movement of the knee in the body of a patient.

The present invention relates to a prosthesis for an anterior cruciate ligament comprising first and second elongate members, first and second tensionable cords, a capture means, and means for securing the elongate members to the femur and tibia, respectively.

The first and second elongate members are inserted into a congruent channel in the femur and tibia, respectively, each member having a longitudinal bore. The first tensionable cord is fixedly attached to the first elongate member and adapted to extend through the bore of the second elongate member, while the second cord is fixedly attached to the second elongate member and is adapted to extend through the bore of the first elongate member. Catch means of the prosthesis are positioned on the bore surface of each elongate member to releasably engage the respective cord which extends through the bore.

The catch means is preferably smooth, rounded projections on the bore to engage the first and second cords. The means for securing the elongate members to the femur and tibia is preferably a stepped cylindrical housing, most preferably coated with a porous material capable of receiving bone tissue ingrowth.

BRIEF DESCRIPTION OF THE DRAWINGS

The invention will be described in detail with reference to a preferred embodiment thereof, which is a anterior cruciate ligament prosthesis. Reference to this embodiment does not limit the scope of the invention, which is limited only by the scope of the claims. In the drawings:

FIG. 1 is an exploded top view of a prosthesis of the invention.

FIG. 2 is a rear elevational view of the device of FIG. 1.

FIG. 3 is a cross sectional view taken along line 3—3 of the device of FIG. 2.

FIG. 7 illustrates the stress-strain characteristics of a normal ligament and the prosthesis of the invention.

DESCRIPTION OF THE PREFERRED EMBODIMENT

Figure 4:
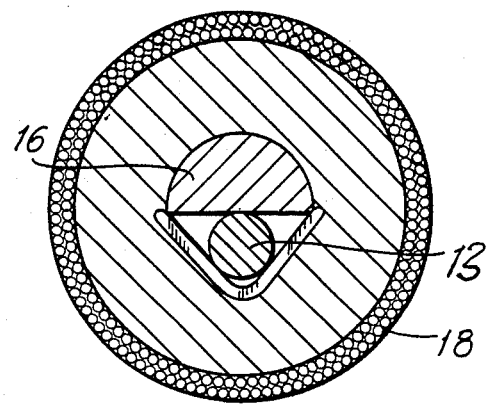
FIG. 4 is a cross sectional view taken along line 4—4 of the device of FIG. 3.

A prosthesis 4 for a ligament of the invention is shown in FIG. 1. Device 4 comprises first and second elongate members 2 and 6 respectively. The elongate members, with a longitudinal bore 8, are inserted into congruent channels 10 in the femur and tibia. The device 4 further includes first and second tensionable cords 12, 13, respectively. The first cord 12 is fixedly attached to the first elongate member 2 and is adapted to extend through the longitudinal bore 8 of the second elongate member 6. The second cord 13 is fixedly attached to the second elongate member 6 and adapted to extend through the longitudinal bore 8 of the first elongate member 2. The cords are preferably ultrasonically welded to secure them to the elongate member to which they are fixedly attached.

A catch means, most preferably smooth rounded projections 20, is located in each of the elongate members 2 and 6 to hold securely the second and first cords 13, 12, respectively. Additionally, a plug 16 with a V-shape is inserted into the bore 8 of each elongate member at the end opposed to the other elongate member. The plug 16 engages the respective cord member which extends through the bore 8 to its associated elongate member, with the plug holding the cord at a desired level of tension. The device further includes a means for securing each of the elongate members to the femur and tibia, respectively. The first and second elongate members 2 and 6, respectively, are preferably made of a surgical implant metal or metal alloy, such as cobalt chrome alloy. The metal or metal alloy parts can be readily manufactured by conventional casting, machining, etc., processes known to those skilled in the art.

The elongate members preferably have two diameters, a narrow diameter for placement in the bone at the intracondular notch and a wider diameter which acts to secure the member to the femoral and tibial end of the bone. The narrow diameter is preferably from about 9 mm. to 15 mm., while the wider diameter is preferably from about 14 mm to 20 mm. The elongate member is further provided with a porous coating 18 to further secure the device 4 by bone ingrowth in the tibial and femoral regions (see FIGS. 5 and 6). The securing means is preferably a step cylinder with the larger diameter being positioned at the insertion end of the femur and tibia, respectively.

The first and second tensionable cords are preferably made of woven implantable polyester material, most preferably Type 55 or Type 56 dacron. Preferably the tensionable cord has a strength of from about 300-900 lbs. with a diameter of from about 0.093 to 0.200 inches. The weave of the material will be preferably standard hollow or solid braid with strand size to range from 10-70 denier. Double weaving of the material is preferable, wherein each strand is braided and the individual braids make the cord weave.

The characteristics of the prosthetic ligament are chosen to match the natural ligament characteristics under low and moderate amounts of stress and strain. As shown in FIG. 7, higher degrees of strain and stress the prosthetic ligament will perform better than the natural ligament. The specific stress strain performance is achieved by a combination of weave type and heat setting.

The first cord 12 is fixedly attached to the first elongate member 2 as shown in FIG. 3, which also shows the device 4 with the catch means engaged. The second cord 13 is securely held in a fixed position, once the tensioning step is completed, by the rounded projections 20, and the plug 16 which is placed in the longitudinal bore 8 on the tibial side of the device. The same procedure is then performed on the femoral side with the first cord 12. In this way the cords are locked once the desired tension is achieved in each of the two cords.

Figure 5:
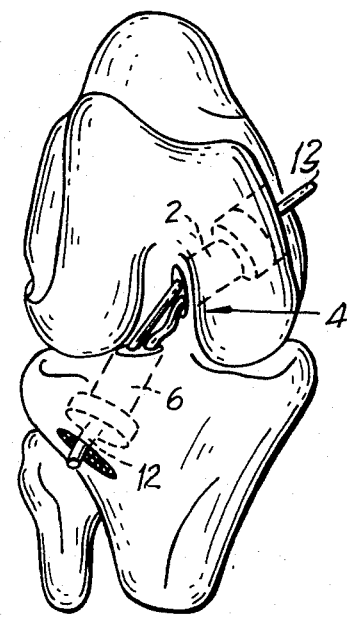
FIGS. 5 and 6 illustrate the prosthesis in FIG. 1 implanted in a patient's knee.
Figure 6:
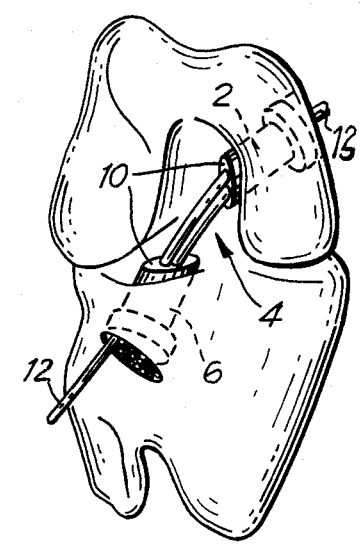

As shown in FIGS. 5 and 6 the first and second elongate members 2, 6 respectively are designed to be positioned so that they are in an oblique angle to one another. This step is important to the successful operation of the prosthetic ligament. The first and second cords are separately tensioned to independently act for flexion and extension. It is important also to the advantageous use of the prosthesis that the elongate member not be allowed to extend beyond the aperture in the osteous tunnel which would cause abrasion of the tissue.

The use of device 4 will be described with reference to the implantation. It is to be understood that a fixation device of the present invention can be used with similar techniques to affix other types of prostheses for the anterior cruciate ligaments (ACL) or other ligaments or tendons, or to affix the same type of prosthesis when used to repair or replace other ligaments or tendons than the ACL. The first step in the procedure is to create two substantially cylindrical through drill holes (note broken lines in FIGS. 5 and 6) in the femur and tibia, insert the second elongate member 6 through the rear end of the tibial drill hole (at the right of the hole in FIGS. 5 and 6) and advance the member therein until the front of the elongate member 6 is flush with the tibial drill hole in the intracondular notch (at the left in FIGS. 5 and 6), and then thread cord 13 sequentially through the femoral drill hole and first elongate member 2 in the direction shown by means of for example, a leader and thread.

The first elongate member 2 is then threaded through the femur in the same manner as on the tibial side. The next step is to pretension the two cords to the desired extent, for example with a conventional pretensioning tool or by hand with the use of an appropriate gauge. Each cord is held in the desired state of pretension wherern the plug 16 is then inserted through the rear end of the appropriate elongate member, in which position cord is firmly held and the tensioning tool is removed. The excess cord is then cut.

Further modifications will occur to those skilled in the art. The scope of the invention is defined by the appended claims and should not be understood as limited by the specific embodiments described herein.

I claim:

1. A prosthesis for a ligament comprising:
   (a) a first and a second longitudinally-bored elongate member for insertion into and securement within a first channel in a femur and a second channel in a tibia, respectively;
   (b) a first and a second separately tensionable cord, the first cord being fixedly attached at one end to the first elongate member and adapted to extend at its other end through the bore of the second elongate member, and the second cord being fixedly attached at one end to the second elongate member and adapted to extend at its other end through the bore of the first elongate member;
   (c) a first and a second means for separately engaging the end of the first cord and the second cord extending through each bore at a desired level of tension; and
   (d) means for securing the first and the second elongate member to the femur and the tibia, respectively.

2. The device of claim 1 wherein the means for engaging comprises projections which engage the first and second cord in the bore of the second or first elongate member, respectively.

3. The device of claim 1 wherein the first and second cords are made of dacron.

4. The device of claim 3 wherein the first and second cords are coated with silicone.

5. The device of claim 1 wherein the means for securing the first and second elongate member to the femur and the tibia, respectively, is a stepped cylindrical elongate member housing adapted to be positioned within the femur and tibia, respectively.

6. The device of claim 5 wherein the housing is coated with a porous material.

* * * * *